United States Patent [19]

Cantrell, Jr. et al.

[11] 4,391,142

[45] Jul. 5, 1983

[54] FREQUENCY TRACKED GATED PULSE TECHNIQUE FOR ULTRASONIC FREQUENCY

[75] Inventors: John H. Cantrell, Jr., Newport News; Joseph S. Heyman, Gloucester, both of Va.

[73] Assignee: The United States of America as represented by the Administrator of the National Aeronautics and Space Administration, Washington, D.C.

[21] Appl. No.: 158,183

[22] Filed: Jun. 10, 1980

[51] Int. Cl.³ .................. G01N 29/00; G01H 9/24
[52] U.S. Cl. .................................. 73/610; 73/602
[58] Field of Search ............. 73/630, 629, 602, 618, 73/659, 609, 610

[56] References Cited

U.S. PATENT DOCUMENTS

| | | | |
|---|---|---|---|
| 2,514,482 | 7/1950 | Farmer | 73/630 |
| 3,815,409 | 6/1974 | Macouski | 73/620 X |
| 3,952,578 | 4/1976 | Jacobs | 73/618 X |
| 4,083,232 | 4/1978 | Heyser et al. | 73/618 |
| 4,135,131 | 1/1979 | Larsen et al. | 324/58.5 A |
| 4,167,879 | 9/1979 | Pedersen | 73/610 |
| 4,217,909 | 8/1980 | Papadofrangakis et al. | 73/602 X |
| 4,271,389 | 6/1981 | Jacobi et al. | 73/602 X |
| 4,301,684 | 11/1981 | Thompson et al. | 73/602 |

OTHER PUBLICATIONS

Hewlett-Packard, 1977 Electronic Instruments and Systems Brochure, Signal Analyzers, Model 141T, 8493A, 8552B.

*Primary Examiner*—Anthony V. Ciarlante
*Assistant Examiner*—David V. Carlson
*Attorney, Agent, or Firm*—Howard J. Osborn; John R. Manning; William H. King

[57] ABSTRACT

A tracking generator 21 is slaved to a spectrum analyzer 23 to produce an input signal having a frequency that follows the frequency of the spectrum analyzer sweeping local oscillator 22. The input signal is gated to a transducer 26 by a transmitter gate 25 to produce ultrasonic waves in the sample 28. The resulting ultrasonic echoes are converted into electrical signals by the transducer and then gated into the spectrum analyzer by receiver gate 29. This arrangement produces spectra that are equivalent to shock-exciting the transducer with a true delta function shock-excitation.

3 Claims, 7 Drawing Figures

MEDIUM 3

FREQUENCY TRACKED GATED PULSE TECHNIQUE FOR ULTRASONIC FREQUENCY

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The invention relates generally to ultrasonic frequency analysis and more specifically concerns ultrasonic frequency analysis which employs frequency tracked gated rf pulses.

In a typical prior art device for obtaining ultrasonic frequency analysis, a short untuned voltage spike from a pulser shock-excites a highly damped piezoelectric transducer. The transducer emits a sharp ultrasonic pulse with a relatively large frequency bandwidth which propagates through a delay line before striking the sample. The return echoes from two different regions of the sample are gated singly or together, depending on the properties to be investigated, into a spectrum analyzer which displays the magnitude of the Fourier transform of the input to the analyzer. In a similar but different prior art device the shock pulser is replaced by a gated rf source with a frequency centered at the resonant frequency of the transducer.

The disadvantages of the prior art devices are: there is modulation of the frequency spectra due to finite pulse widths; large amplitude drive voltages are required which produce nonlinearities in the signal emitted by the transducer and which contributes to the problem of electronic rise time and amplifier saturation; and errors are caused by receiver gate width or position.

It is therefore an object of this invention to eliminate modulation of the frequency spectra due to finite pulse widths in ultrasonic frequency analysis.

Another object of this invention is to lower the instantaneous drive power required for the transducers in ultrasonic frequency analysis, and thereby decrease the disadvantages associated with large amplifier drive voltages.

A further object of this invention is to decrease the errors due to receiver gate width or position in ultrasonic frequency analysis.

Other objects and advantages of this invention will become apparent hereinafter in the specification and drawings.

SUMMARY OF THE INVENTION

A tracking generator is slaved to a spectrum analyzer to produce a signal having a frequency that follows the frequency of the spectrum analyzer sweeping local oscillator. A transducer is attached to the sample to be analyzed. The transducer produces ultrasonic waves in the sample in response to electrical signals applied to the transducer, and the transducer produces electrical signals in response to the ultrasonic waves reflected by the sample. A transmitter gate is connected between the tracking generator and the transducer, and a receiver gate is connected between the transducer and the spectrum analyzer. A logic timing generator is connected to the transmitter gate and the receiver gate for controlling the pulse transmitting and receiving sequence, the pulse width, and the pulse repetition rate. This arrangement locks the frequency of the rf input pulse gated to the spectrum analyzer to the frequency in the analyzer at which measurements are being made. This produces spectra that are equivalent to shock-exciting the transducer with a true delta function shock-excitation. In addition, since the drive voltages are typically two orders of magnitude lower than that of conventional methods, unwanted nonlinearities in the emission spectra are eliminated.

DETAILED DESCRIPTION OF THE INVENTION

Figure 1:
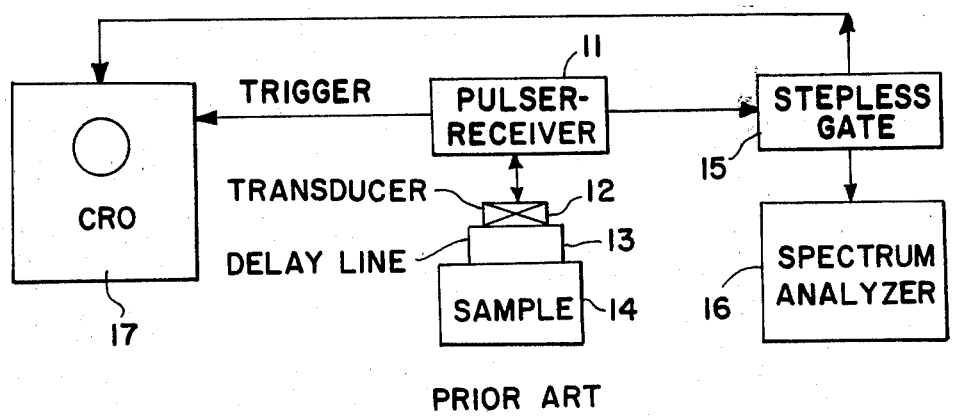
FIG. 1 is a block diagram of a prior art device for ultrasonic frequency analysis.

A typical prior art single transducer apparatus arrangement for ultrasonic pulse spectrum analysis is shown in FIG. 1. A short untuned voltage spike from a pulser receiver 11 shock-excites a highly damped piezoelectric transducer 12. The highly damped transducer 12 emits a sharp ultrasonic pulse with a relatively large frequency bandwidth which propagates through a delay line 13 (liquid or solid) before striking a sample 14. The returning echoes from two different regions of the sample are gated singly or together, depending on the properties to be investigated by a stepless gate 15 into a spectrum analyzer 16. The spectrum analyzer displays the magnitude of the Fourier transform of the input signal. The returning echoes are also gated into a cathode ray oscilloscope 17 by gate 15.

Figure 2:
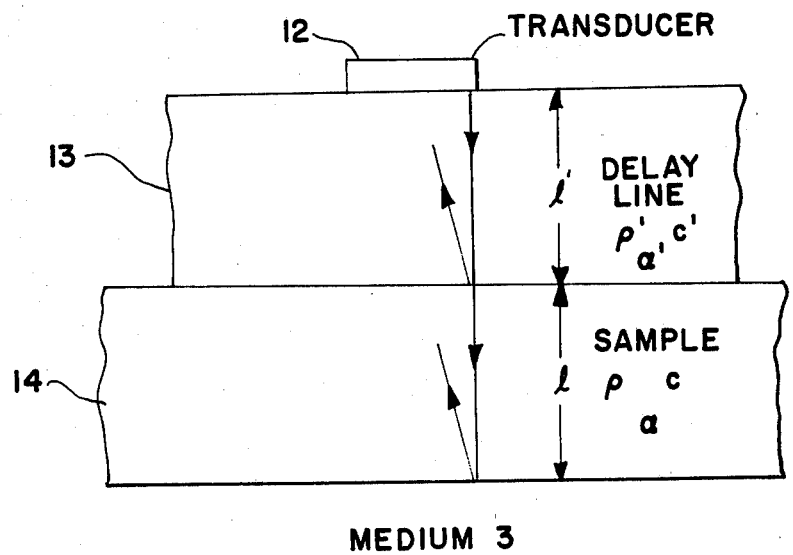
FIG. 2 is a schematic drawing for the purpose of explaining the benefits of this invention.

Let the ultrasonic signal initially emitted by the transducer be f(t) which has a Fourier transform defined by $$g(\omega) = (2\pi)^{-\frac{1}{2}} \int_{-\infty}^{\infty} f(t)e^{-j\omega t}dt = F[f(t)] \tag{1}$$

where t is the time and $\omega$ is the angular frequency. As shown in FIG. 2, the signal propagates with velocity c' through the delay line having an attenuation coefficient $\alpha'$ and is reflected at the interface of the delay line 13 and the sample 14 after traveling a distance l'. Generally, the pulse propagation time through the delay line is at least twice the pulse propagation time through the sample to permit echoes from within the sample to return to the transducer without interference from echoes reverberating in the delay line.

If the gate 15 is adjusted such that only the echo $f_1(t)$ from the delay line sample interface is received by the spectrum analyzer 16, the spectrum displayed by the analyzer will be given by $$|g_1(\omega)| = |F[f_1(t)]| \qquad (2)$$

In terms of the Fourier transform of the initial signal f(t)

$$|g_1(\omega)| = R_{12}e^{-2\alpha' l'}|g(\omega)| \qquad (3)$$

where $R_{12}$ is the magnitude of the reflection coefficient at the interface and $|g(\omega)|$ is obtained from equation (1).

Similarly, if the gate 15 is adjusted such that only the echo $f_2(t)$ from the interface of the sample and medium 3 (e.g. air) is received, the spectrum displayed by the analyzer will be $$|g_2(\omega)| = |F[f_2(t)]| = T_{12} T_{21} R_{23} e^{-2(\alpha' l' + \alpha l)}|g(\omega)| \qquad (4)$$

where $T_{12}$ is the magnitude of the transmission coefficient at the delay line-sample interface when the pulse is propagating in the forward direction, $T_{21}$ that for propagation in the backward direction, and $R_{23}$ the magnitude of the reflection coefficient at the sample-medium 3 interface. $\alpha$ is the attenuation coefficient for the sample length l.

Comparing equations (3) and (4) reveals that the Fourier Transforms of pulses $f_1(t)$ and $f_2(t)$ are related by $$|g_2(\omega)| = \left[\frac{T_{12}T_{21}R_{23}}{R_{12}}\right][e^{-2\alpha l}|g_1(\omega)|] = k(\omega)|g_1(\omega)| \qquad (5)$$

where $k(\omega)$ is a real function. Thus, $f_2(t)$ is the convolution of $f_1(t)$ with the Fourier transform of $k(\omega)$. Note that $k(\omega)$ is functionally dependent on the attenuation coefficient of the sample.

Consider now the case where the time domain signals $f_1(t)$ and $f_2(t)$ are gated simultaneously into the spectrum analyzer. Since the signals are separated $2t_o$ in time, it is convenient to write $f_1(t+t_o)$ for signal from the delay line-sample interface and $f_2(t-t_o)$ for the signal from the sample-medium 3 interface. Using the Fourier transform property $$F[f(t \pm t_o)] = e^{\pm j\omega t_o} g(\omega) \qquad (6)$$

the spectrum displayed by the spectrum analyzer is now $$|F[f_1(t+t_o) + f_2(t-t_o)]| = |e^{j\omega t_o}g_1(\omega) + e^{-j\omega t_o}g_2(\omega)| = \qquad (7)$$
$$\{[1-k(\omega)]^2 + 4k(\omega)\cos^2\omega t_o\}^{\frac{1}{2}}|g_1(\omega)|.$$

Comparing equations (2) and (7) shows that the spectrum is that of the Fourier transform of the first pulse, $f_1(t)$, modulated by a factor which depends on $k(\omega)$.

For the case $k(\omega) = 1$, $f_1(t) = f_2(t)$ and equation (7) reduces to $$|F[f_1(t+t_o) + f_1(t-t_o)]| = |2\cos \omega t_o||g_1(\omega)|. \qquad (8)$$

In this case the modulation is simply a series of maxima and minima that depend on $t_o$. If $|g_1(\omega)|$ is a slowly varying function of $\omega$ relative to $\cos \omega t_o$, the maxima of equation (8) may be approximated by the maxima of $|2\cos \omega t_o|$ which occur at $$\omega t_o = n\pi, n = 0, \pm 1, \pm 2, \ldots \text{ or } \nu_n = \frac{n}{2t_o} \qquad (9)$$

where $\nu = \omega/2\pi$. The separation of the frequency maxima is $$\Delta \nu = \frac{1}{2t_o}. \qquad (10)$$

Thus, the maxima (or minima) of the spectrum depend on the time separation $2t_o$ of the pulses $f_1(t+t_o)$ and $f_1(t-t_o)$ simultaneously gated into the spectrum analyzer. This information may be used to calculate the ultrasonic velocity c of the sample according to the relation $$c = \frac{l}{t_o} = 2l\Delta\nu. \qquad (11)$$

The modulation factor in equation (7) is similar to that of equation (8) except that the minima do not extend to zero for $k(\omega) \neq 1$. However, equation (11) may still be used for calculating the ultrasonic velocity.

As seen from equation (1) the shape of the time domain function f(t) determines the range over which frequency information can be obtained. Theoretically, a delta function shock-excitation of an ideal transducer gives rise to the broadest possible ultrasonic frequency spectrum since the Fourier transform of a delta function is a nonzero constant for all frequencies. Practically, such a situation cannot be realized since (1) all electronic circuits have finite risetimes (i.e., finite pulse width) and (2) the electroacoustic transfer function for piezoelectric transducers and connecting circuits/cables is not unity (each transducer has a characteristic frequency profile).

Figure 3:
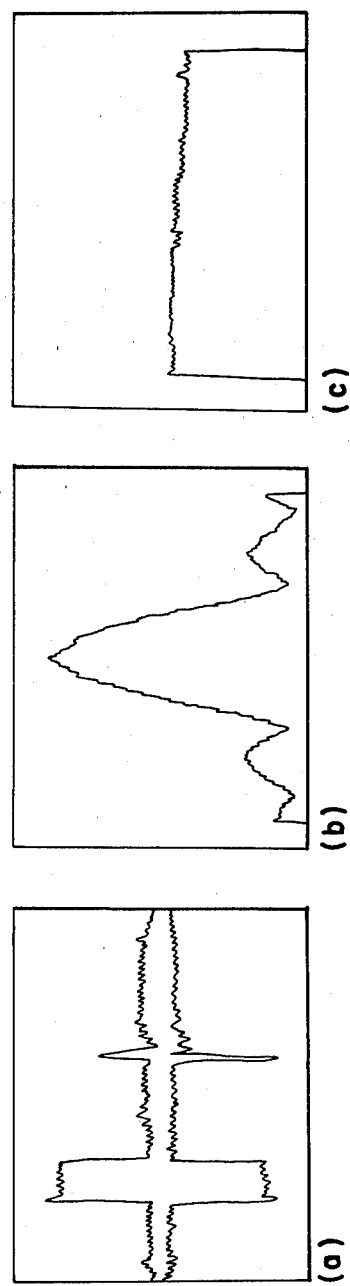
FIG. 3 shows an input and two different outputs from a spectrum analyzer for the purpose of explaining the benefits of this invention.

In order to investigate the implications to spectrum analysis of a finite pulse width, consider the case of a pulsed rf signal of time duration 2T and frequency $\omega'$ centered at the resonant frequency of the transducer. We assume that the transducer generates an ultrasonic signal f(t) of the same time duration and frequency. The apparatus arrangement is the same as in FIG. 1 except that the shock pulser is replaced by a gated rf source. FIG. 3(b) shows the spectrum obtained by gating into the spectrum analyzer the first return signal (shown in FIG. 3(a)). The trailing spike in FIG. 3(a) is gate feed-through. The modulation in the spectrum results primarily from the finite width of the rf pulse and is analogous to the optical diffraction pattern of a finite slit.

For simplicity, let us assume that $f_1(t) = f(t)$. Mathematically, the rf pulse is represented as $$f_1(t) = \begin{cases} E\cos(\omega't + \theta), & -T \leq t \leq T \\ 0, & |t| > T \end{cases} \qquad (12)$$

where E is the amplitude of the pulse and $\theta$ is an arbitrary phase. The magnitude of the Fourier transform of equation (12) is then $$|g_1(\omega)| = \frac{ET}{\sqrt{2\pi}} = \left\{ \left(\frac{\sin(\omega'-\omega)T}{(\omega'-\omega)T}\right)^2 + \qquad (13) \right.$$

-continued $$\left(\frac{\sin(\omega' + \omega)T}{(\omega' + \omega)T}\right)^2 +$$

$$2\frac{\sin(\omega' - \omega)T}{(\omega' - \omega)T}\frac{\sin(\omega' + \omega)T}{(\omega' + \omega)T}\cos 2\theta \biggr\}^{\frac{1}{2}}$$

The first two terms on the right-hand side of equation (13) are identical to the functional form of two single slit optical diffraction patterns centered at $\omega = \omega'$ and $\omega = -\omega'$, respectively. Each pattern has a central maximum and many secondary maxima. The last term in equation (13) is a cross-term due to the phase $\theta$ of the pulse.

If $\omega'T \geq 50$, the amount of amplitude interference in the central maximum of either pattern due to the presence of the other, or from the cross-term in equation 13, is less than 1%. Using this condition and the fact that the spectrum analyzer sweeps only through non-negative values of frequency, we may write equation (13) as $$|g(\omega)| \simeq \frac{ET}{\sqrt{2\pi}} \left| \frac{\sin(\omega' - \omega)T}{(\omega' - \omega)T} \right|, \omega \geq 0 \quad (14)$$

to a good approximation for $\omega \geq 0$. In all experiments reported in this specification the pulse width is 10 μsec and $f'(=\omega'/2\pi)$ is 5.75 MHz. This gives an amplitude interference in the central maximum of less than 0.3%.

As the pulse width is decreased the separation of the minima of equation (14) increases. In the limit of infinitesimal pulse width, the broad spectral characteristics of a delta function shock-excitation is approached. However, unless the amplitude of the pulse increases as the width decreases, there is less total energy into the ultrasonic pulse to be distributed over the frequency range. Typical ultrasonic shock pulses are driven with 300 V electrical spikes. The finite risetime of the electrical spikes coupled with the electracoustic transfer characteristics of the transducer limits the extent to which the ideal situation is realized with shock-excited systems.

Figure 4:
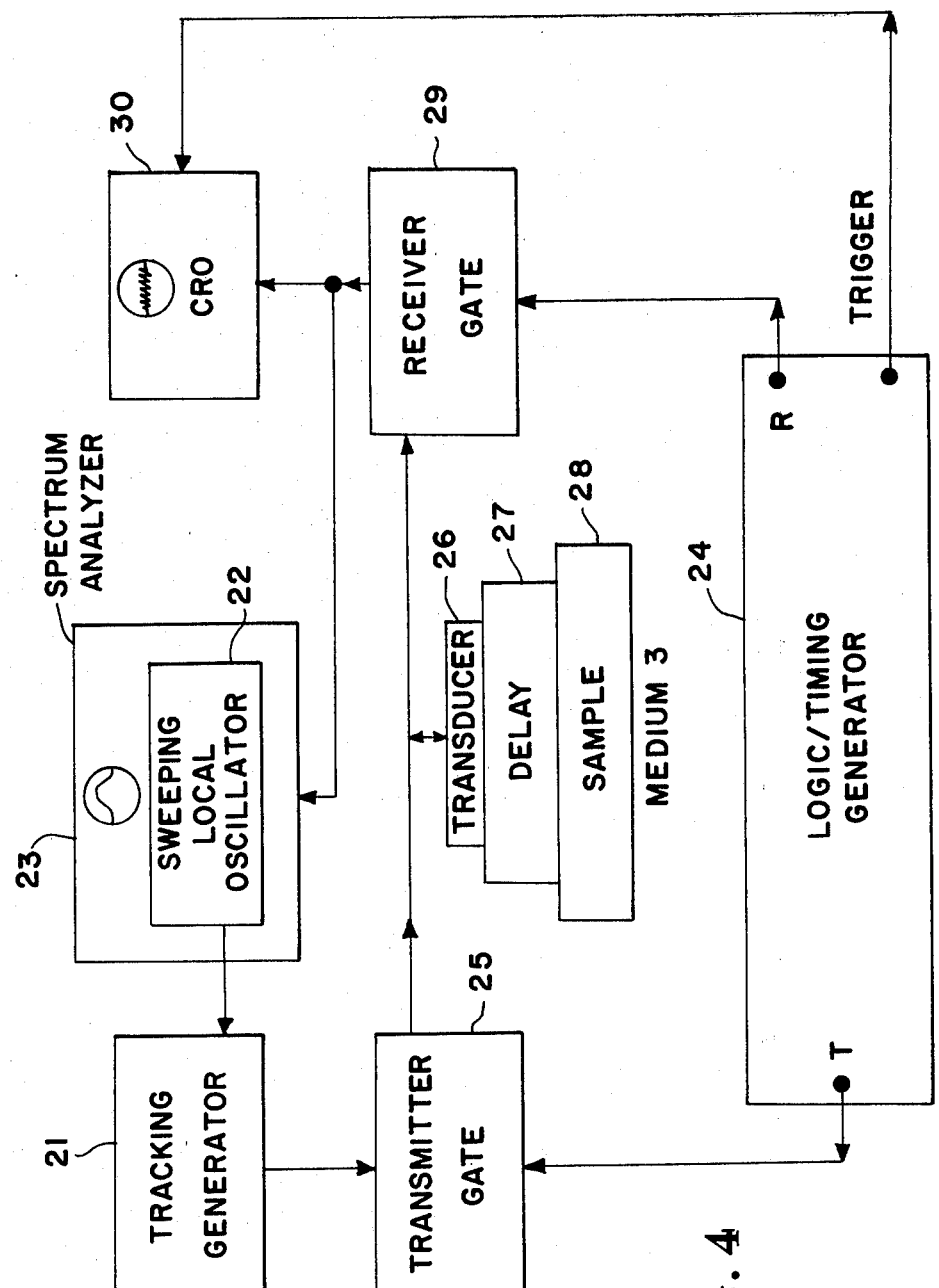
FIG. 4 is a block diagram of the preferred embodiment of this invention.

Turning now to the embodiment of the invention selected for illustration in FIG. 4 of the drawings, the number 21 designates a tracking generator. Tracking generator 21 is slaved to the sweeping local oscillator 22 of a spectrum analyzer 23 so that the output frequency of the tracking generator is allowed to track the local oscillator frequency. A logic-timing generator 24 which is used to control the pulse transmission and receiving sequence, the pulse width, and the pulse repetition rate, applies a signal to a transmitter gate 25 which allows the output of tracking generator 21 to be applied to a transducer 26. The resulting ultrasonic signals produced by the transducer travel through a delay 27 and a sample 28. The echoes from the delay sample interface and the sample-medium 3 interface are converted to electrical signals by transducer 26 and then applied to a receiver gate 29. A trigger signal from generator 24 turns on a cathode ray oscilloscope 30 and another signal from generator 24 is applied to receiver gate 29, which applies the echo signals to both spectrum analyzer 23 and oscilloscope 30. Logic/timing generators are well known and therefore generator 24 is not disclosed in detail in this specification.

Figure 5:
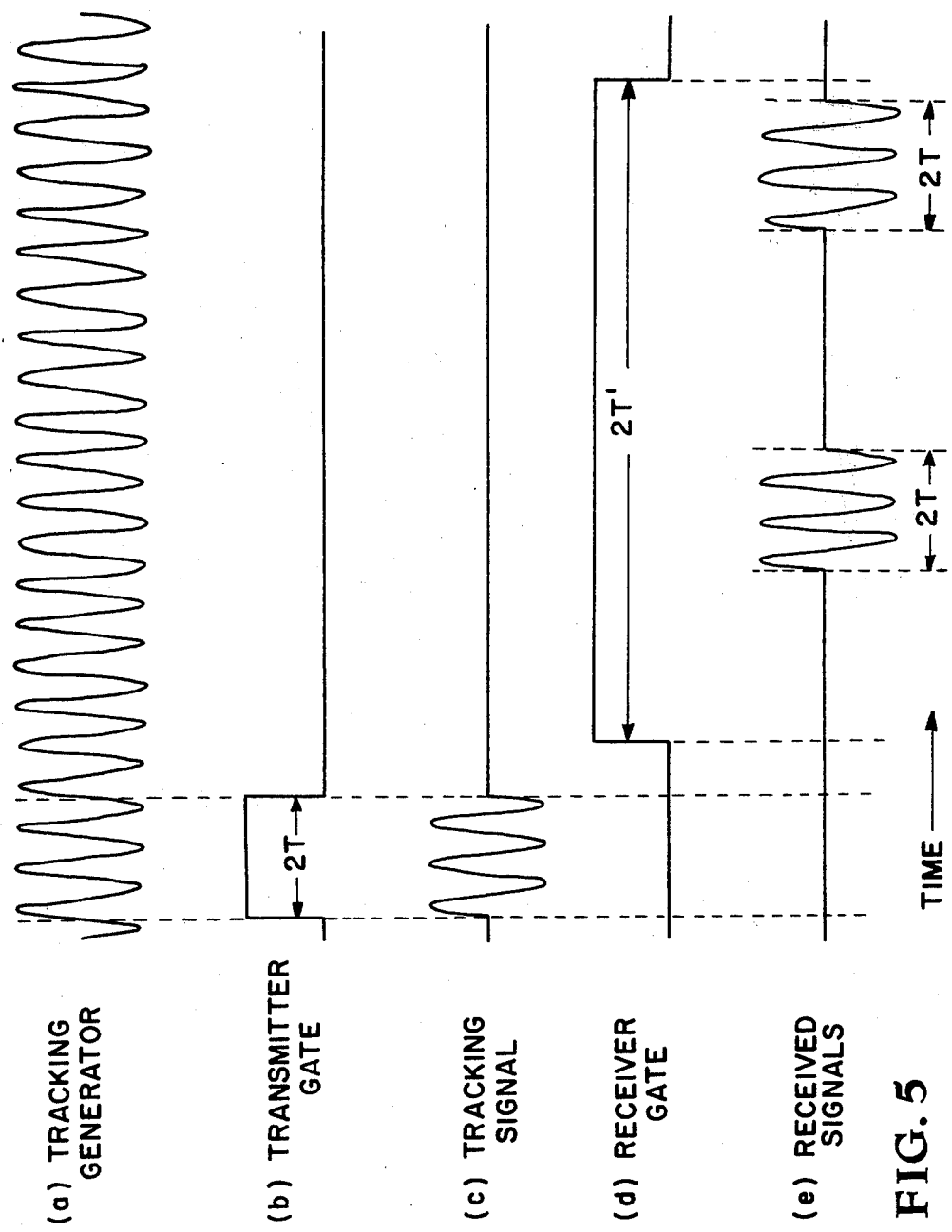
FIG. 5 is a signal timing diagram for the preferred embodiment of this invention.

A signal timing diagram of the system of FIG. 4 is shown in FIG. 5. The rf output of tracking generator 21 (FIG. 5(a)) is connected to transmitter gate 25 with an on-to-off ratio of approximately 90 dB. The transmitter gate is turned on for time 2T (FIG. 5(b)) and produces an rf pulse which excites transducer 26. The transducer emits an ultrasonic tone-burst (FIG. 5(c)) which propagates through delay line 27 into sample 28. Selected echoes from the sample (FIG. 5(e)) are obtained for spectrum analysis by turning on receiver gate 29 for the appropriate time 2T' (FIG. 5(d)). The output of the receiver is viewed with oscilloscope 30 for time domain measurements and with spectrum analyzer 23 for frequency domain measurements.

Setting the pulse width equal to 10 μsec yields the spectrum shown in FIG. 3(c). The frequency modulation introduced by the finite pulse width is now removed. The reason is that the spectrum analyzer measures the input signal strength within a set bandwidth (usually adjustable) and sweeps the center frequency of the bandwidth to generate a spectrum plot. The frequency tracking technique locks the frequency of the rf input pulse gated to the spectrum analyzer to the center frequency of the bandwidth being measured. Mathematically, this is equivalent to setting $\omega' = \omega$ in equation (14). Hence, $$|g_1(\omega)|_{\omega=\omega'} = \frac{ET}{\sqrt{2\pi}} \left| \frac{\sin(\omega' - \omega)T}{(\omega' - \omega)T} \right|_{\omega=\omega'} = \frac{ET}{\sqrt{2\pi}} \quad (15)$$

Since 2T, the pulse width, and E, the pulse amplitude, are constants, equation (4) shows that $|g_1(\omega)|$ is frequency independent, verifying the result of FIG. 3(c).

Figure 6:
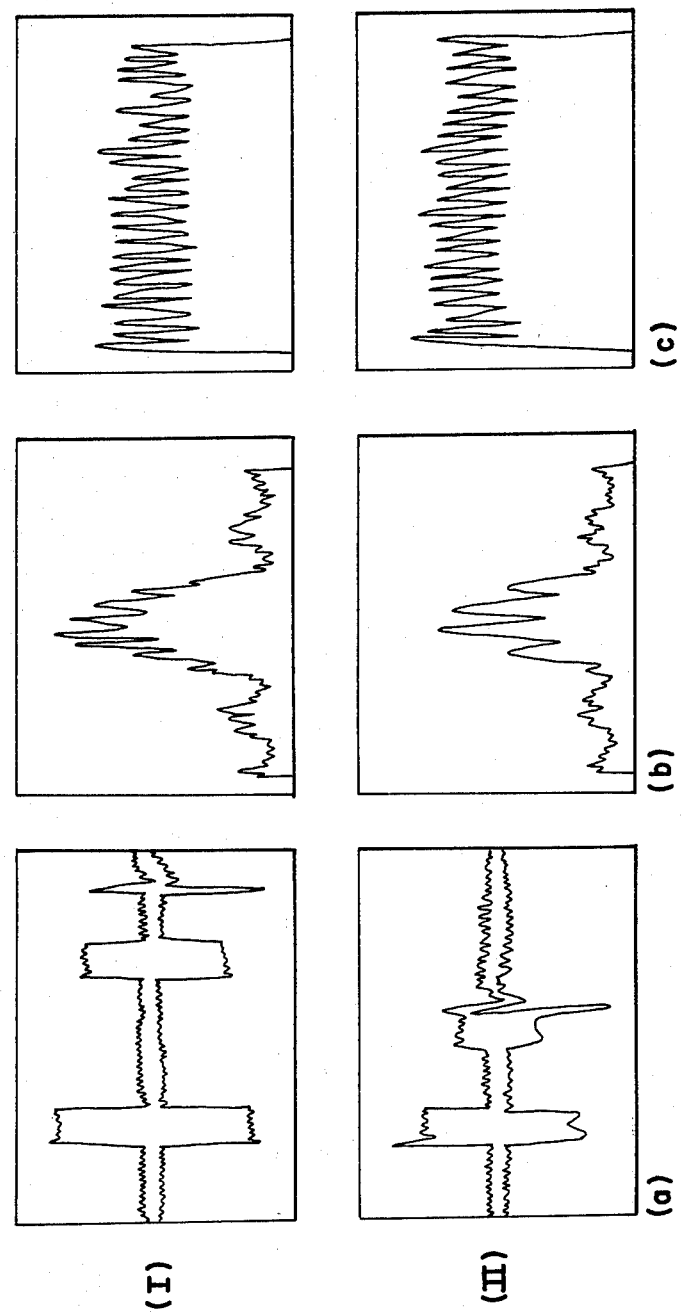
FIG. 6 shows inputs to and outputs from a spectrum analyzer for the purpose of explaining the benefits of this invention.

In the echo from the delay line-sample interface and the echo from the sample-medium 3 interface are gated simultaneously into the spectrum analyzer, the results shown in FIG. 6 are obtained. The Figure is broken into two rows and three columns. Column (a) shows the input to the spectrum analyzer. Column (b) displays the spectra obtained by conventional spectrum analysis using fixed rf pulses as described above. Column (c) shows the spectra resulting from the frequency tracking technique. As expected, the frequency modulation of the spectra due to a finite pulse width are removed by the frequency tracking technique.

Consider now the individual rows. The results of row I are obtained by gating simultaneously into the spectrum analyzer two echoes, each of width 2T, separated in time by $2t_o$. The frequency separation of the maxima in column (c) and also in column (b) (ignoring the modulation due to finite pulse width) is given by equation (10) and can be used to calculate the ultrasonic velocity of the sample according to equation (11).

Figure 7:
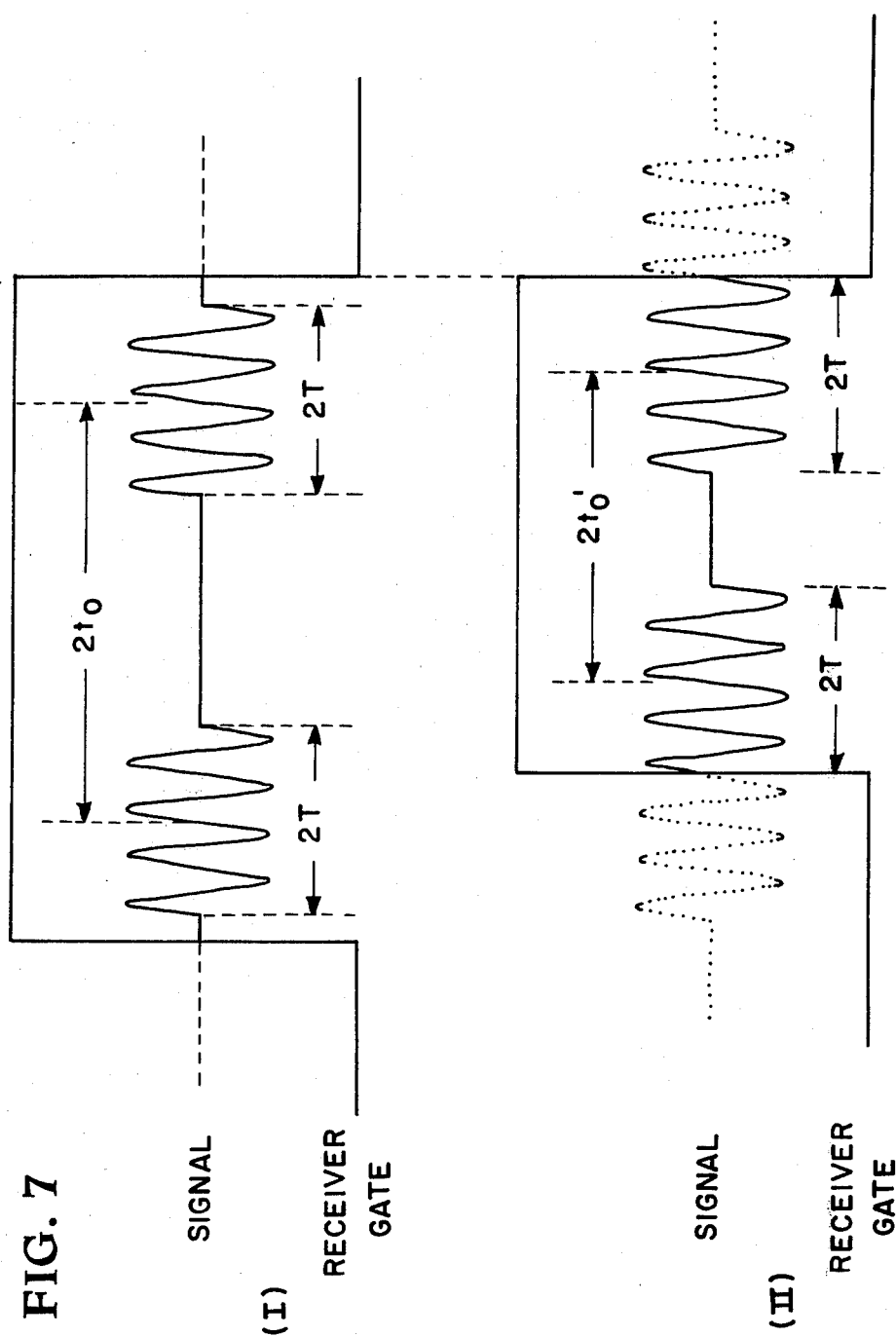
FIG. 7 shows two different input signals to the transducer and two different receiver gate durations for the purpose of explaining a benefit of this invention.

The results of row II are obtained by increasing the pulse width, and adjusting the width and position of the receiver gate to the spectrum analyzer such that the input to the analyzer consists of two pulses each of width 2T, as before, but now separated in time by $2t_o'$. The situation is illustrated in FIG. 7. As expected, the spectrum displayed by the conventional method in column (b) of FIG. 6 indicates the change in pulse separation time. The frequency separation of the maxima are now given by $\Delta f' = (2t_o')^{-1}$. If this frequency separation were used to calculate the ultrasonic velocity of the sample according to equation (11), the value would be in error.

In contrast, the spectra displayed by the frequency tracking technique in column (c) of FIG. 6 reveals no difference in the spectra of cases I and II, and either spectrum may be used to correctly calculate the ultrasonic velocity. The explanation lies in the relative phase modulation experienced by the two input pulses of case II when the frequency tracking technique is used. Reference to FIG. 7 indicates that the first pulse of case II suffers a phase shift of $$\phi(\omega') = 2\omega'(t_o - t'_o) \quad (16)$$

relative to the second pulse. It must be emphasized that this phase shift results from the particular width and position of the receiver gate—not from the sample itself. The magnitude of the Fourier transform of the two pulses, assuming $f_1(t) = f_2(t)$ for simplicity, is then $$|F[e^{j\phi(\omega')}f_1(t + t'_o) + f_1(t - t'_o)]| = \quad (17)$$

$$\left| 2 \cos\left(\omega t'_o + \frac{\phi(\omega')}{2}\right) \right| |F[f_1(t)]|$$

Equation (17) explains the spectra for case II observed in column (b) and in column (c) of FIG. 6.

For the conventional method depicted for case II in column (b) of FIG. 6 $\phi(\omega')$ is constant and the frequency maxima occur at $$\nu'_n = \frac{n + \frac{\phi}{2\pi}}{2t'_o}, \quad n = 0, \pm 1, \pm 2, \ldots \quad (18)$$

The separation of the frequency maxima is given by $$\Delta \nu' = \frac{1}{2t'_o} \quad (19)$$

as observed.

When the frequency tracking technique is used [FIG. 6(c)], $\phi(\omega')$ is no longer constant since $\omega' = \omega$, and equation (17) becomes $$|F[e^{j\phi(\omega')}f_1(t + t'_o) + f_1(t - t'_o)]|_{\omega = \omega'} = \quad (20)$$

$$|2 \cos \omega t_o| \; |F[f_1(t)]|_{\omega = \omega'} = |2 \cos \omega t_o| \sqrt{\frac{ET}{2\pi}}$$

The separation of the frequency maxima predicted by equation (20) is given by equation (10) and is the same as that predicted by equation (8) for case I. In addition, equation (20) shows that the frequency modulation due to the finite pulse width is removed by the frequency tracking technique as prescribed by equation (15). Further experiments show that the same separation of the frequency maxima occur with the frequency tracking technique regardless of the widths, amplitudes, or positions of the two individual successive pulses provided any portion of each pulse is gated simultaneously into the spectrum analyzer. Thus, the frequency tracking technique allows correct velocity measurements to be made in a sample even though the receiver gate position is not optimized and the frequency modulation due to the electronic risetime is unknown.

Ultrasonic spectrum analysis by frequency tracked gated rf pulses exhibits several advantages over conventional pulse techniques. Among these are:

(1) Modulation of the frequency spectra due to the finite pulse width is eliminated in the spectral range of interest. Finite pulse widths are inherent to all shock-excited spectrum analysis systems because of risetime limitations of the electronics. The frequency tracking technique produces results equivalent to exciting the transducer with a delta function shock pulse.

(2) The frequency tracking technique allows the frequency spectrum to be generated with lower instantaneous drive power to the transducer than does the conventional method since shock excitation is not used with the frequency tracking technique. Large amplitude drive voltages produce nonlinearities in the signal emitted by the transducer which would not be present with the lower drive voltages of the frequency tracking technique. In addition, the use of large voltage spikes with the conventional method contributes to the problem of electronic risetime and amplifier saturation.

(3) The frequency tracking technique permits ultrasonic velocity measurements in a sample to be made without regard to receiver gate width or position provided any portions of at least two successive echoes are gated simultaneously into the spectrum analyzer.

(4) One further advantage not previously addressed is to use the frequency tracking technique with the newly developed acoustoelectric transducer (AET) U.S. Pat. No. 4,195,244. The AET, unlike conventional transducers, is insensitive to phase variations across the ultrasonic wavefront and, thus, permits accurate data to be obtained on samples that are inhomogeneous or possess irregular geometry. The electrical output of the AET is a dc signal level which is proportional to the total acoustic flux (acoustic energy per unit area per unit time) incident on the device. Since the dc output does not distinguish between acoustic fluxes of different frequencies, broadband shock pulses of conventional methods cannot be used with the AET to extract information. However, when the AET is used with the frequency tracking technique the dc level is defined at the tracking frequency, and, therefore, does permit a power spectrum to be generated. Experiments have shown that clean spectral information is obtained with the AET even when sample inhomogeneity and geometrical irregularity severely degrades the spectral output obtained with conventional piezoelectric transducers.

The practical limitations of the frequency tracking technique are associated with the frequency limitations of the spectrum analyzer and the electroacoustic bandwidth characteristics of the transducer. For most ultrasonic measurements the spectrum analyzer imposes little limitation since they typically have bandwidths in the tens of hundreds of megahertz. With regard to the electroacoustic bandwidth characteristics, most transducers used in ultrasonic spectrum analysis are piezoelectric and have bandwidths of the order of 5 to 7 megahertz. The development of broadband capacitive transducers, however, should eliminate this restriction, thereby permitting maximum exploitation of the frequency tracking technique for ultrasonic frequency analysis.

It is to be understood that the form of the invention herewith shown and described is to be taken as a preferred embodiment. Various changes may be made without departing from the invention. For example, transducers can be located on both sides of the sample with one being an input transducer and the other being an output transducer.

What is claimed is:

1. A device for obtaining an ultrasonic frequency analysis comprising:

a spectrum analyzer having a tuning frequency;

a tracking generator means connected to said spectrum analyzer for producing an RF source locked to the tuning frequency of said spectrum analyzer;

a transducer means suitable for attachment to the sample to be frequency analyzed;

a transmitter on-off gate connected between said tracking generator means and said transducer means;

a receiver on-off gate connected between said transducer means and said spectrum analyzer; and circuit means connected to said transmitter gate and said receiver gate for gating pulses of the RF signal from the tracking generator to the transducer means through the transmitter gate and for gating selected durations not coinciding with the durations of said pulses the resulting echo signals from the transducer means to the spectrum analyzer through the receiver gate.

2. A device for obtaining an ultrasonic frequency analysis according to claim 1 including an oscilloscope connected to the output of said receiver gate to provide time domain measurements.

3. A device for obtaining an ultrasonic frequency analysis according to claim 1 wherein said spectrum analyzer includes a sweeping local oscillator that said tracking generator means is connected to for producing an RF source locked to the tuning frequency of the spectrum analyzer.

* * * * *